(12) United States Patent
Zou et al.

(10) Patent No.: US 11,642,388 B2
(45) Date of Patent: May 9, 2023

(54) ANTIDEPRESSANT COMPOUND PREPARATION AND PREPARATION METHOD THEREOF

(71) Applicants: Chenland Nutritionals Inc., Pomona, CA (US); Qingdao Chenland Pharmaceutical Technology Development Co., Ltd., Qingdao (CN)

(72) Inventors: Shengcan Zou, Qingdao (CN); Jiancheng Zong, Qingdao (CN); Wenyu Li, Qingdao (CN); Lei Zong, Qingdao (CN); Zengliang Zhang, Qingdao (CN); Shanglong Wang, Qingdao (CN)

(73) Assignees: CHENLAND NUTRITION ALS INC., Pomona, CA (US); QINGDAO CHENLAND PHARMACEUTICAL TECHNOLOGY DEVELOPMENT CO., LTD., Qingdao (CN)

( * ) Notice: Subject to any disclaimer, the term of this patent is extended or adjusted under 35 U.S.C. 154(b) by 132 days.

(21) Appl. No.: 17/105,628

(22) Filed: Nov. 26, 2020

(65) Prior Publication Data
US 2022/0160807 A1    May 26, 2022

(51) Int. Cl.
*A61K 36/744* (2006.01)
*A61K 36/185* (2006.01)
*A61K 36/65* (2006.01)
*A61P 25/24* (2006.01)
*A61K 36/48* (2006.01)

(52) U.S. Cl.
CPC .......... *A61K 36/744* (2013.01); *A61K 36/185* (2013.01); *A61K 36/48* (2013.01); *A61K 36/65* (2013.01); *A61P 25/24* (2018.01); *A61K 2236/31* (2013.01); *A61K 2236/333* (2013.01); *A61K 2236/39* (2013.01)

(58) Field of Classification Search
None
See application file for complete search history.

*Primary Examiner* — Terry A McKelvey
*Assistant Examiner* — Catheryne Chen
(74) *Attorney, Agent, or Firm* — Daniel M. Cohn; Howard M. Cohn

(57) ABSTRACT

An antidepressant compound preparation and a preparation method for same were disclosed, The antidepressant includes the following raw materials of *Hypericum perforatum* L., *Paeonia lactiflora* Pall., *Gardenia jasminoides* Ellis, *Albizia julibrissin* Durazz. and *Moutan cortex*. The raw materials are weighed in proportion to obtain extracts respectively, and the extracts are mixed to prepare a compound preparation. The compound preparation prepared by the present invention has the advantages of simple preparation, safety, low toxic and side effects, no dependence, etc., and can effectively alleviate depression mood.

1 Claim, No Drawings

ANTIDEPRESSANT COMPOUND PREPARATION AND PREPARATION METHOD THEREOF

TECHNICAL FIELD

The present invention relates to the technical field of traditional Chinese medicine compound compositions, and more particularly to an antidepressant compound preparation and a preparation method therefor.

BACKGROUND

In real life, due to the fast pace of life, high working and economic pressures, and other reasons, it is easy to cause depression mood. Depression mood, as a common mood disorder disease, is an affective disorder disease with low mood as the main symptom and corresponding thinking and behavior changes, has the clinical manifestations including low mood, retardation of thinking, decreased appetite, sleep disorder, etc., which seriously endanger people's physical and mental health. Severe depression mood can develop into depression and even suicide. It is believed in traditional Chinese medicine that depression mood is mostly induced by emotions such as depression, anger, worry, sorrow and sadness. The etiology is gloomy mood and internal organ stasis which cause qi movement disorder of the five internal organs, thereby resulting in various mental symptoms.

At present, most of the medicines used for treating depression are Western medicines, which are mainly prepared by chemical synthesis and have obvious curative effect. However, the Western medicines have the disadvantages such as high toxic and side effects, addiction, high price and easy recurrence. In addition, long-term use of the Western medicines will have certain side effects, and will also make the viruses and bacteria in the body immune to such medicines. Western medicines are mostly chemical preparations, which are very useful in initial treatment, but are prone to cause drug resistance after long-term use. As the metabolism of the medicines mainly depends on the liver, taking Western medicine for a long time will put certain pressure on the liver and the kidneys, which directly affects people's physical and mental health, and directly brings mental and economic burdens to patients and families.

In a traditional Chinese medicine treatment method, traditional Chinese medicine compound preparations for smoothing the qi movement of the liver, restoring liver function, calming the nerves, nourishing the heart, invigorating heart and spleen, and nourishing the liver and kidney are commonly and mostly used in clinic. Certain progress is made for single-ingredient traditional Chinese medicines in the treatment of depression; however, due to the fact that depression has multiple causes, unclear etiology and complex pathogenesis, and a single-ingredient traditional Chinese medicine has a single curative effect, clinical symptom improvement time is prolonged and adverse reaction is great, which limits the application. Whereas a traditional Chinese medicine compound has many chemical components which can interact with each other, is safe, and has no toxic or side effect. Therefore, the research of traditional Chinese medicine preparations in the treatment of depression has attracted more and more attention from experts at home and abroad. The present invention seeks an antidepressant traditional Chinese medicine composition with low toxicity, high curative effect and reasonable price from traditional Chinese herbal medicines, which is composed of *Hypericum perforatum* L., *Paeonia lactiflora* Pall., *Gardenia jasminoides* Ellis, *Moutan cortex*. and *Albizia julibrissin* Durazz., and provides a scientific compatibility and preparation method for the traditional Chinese medicine composition and an application thereof in treating depression mood.

Therefore, with respect to the above problems, the problem to be urgently solved by those skilled in the art is to provide an antidepressant compound preparation and a preparation method therefor.

SUMMARY

In view of this, the present invention provides an antidepressant compound preparation and a preparation method therefor, wherein the compound preparation has the advantages of simple preparation, safety, low toxic and side effects, no dependence, etc., and can effectively alleviate depression mood.

To achieve the above purpose, the present invention adopts the following technical solution:

An antidepressant compound preparation, composed of the following raw materials in parts by weight: 10-50 parts of *Hypericum perforatum* L., 100-150 parts of *Paeonia lactiflora* Pall., 10-100 parts of *Gardenia jasminoides* Ellis, 50-300 parts of *Albizia julibrissin* Durazz. and 50-200 parts of *Moutan cortex*.

Preferably, the antidepressant compound preparation is composed of the following raw materials in parts by weight: 30 parts of *Hypericum perforatum* L., 120 parts of *Paeonia lactiflora* Pall., 60 parts of *Gardenia jasminoides* Ellis, 100 parts of *Albizia julibrissin* Durazz. and 100 parts of *Moutan cortex*.

A preparation method for the antidepressant compound preparation, comprising the following specific steps:

S1: weighing *Hypericum perforatum* L., *Paeonia lactiflora* Pall., *Gardenia jasminoides* Ellis, *Albizia julibrissin* Durazz. and *Moutan cortex* in proportion to prepare materials;

S2: adding the *Hypericum perforatum* L. into a 70% ethanol aqueous solution with a volume ratio of material to liquid being 1:8, extracting twice for 1.5 hours each time, merging the extracting solutions, filtering, reclaiming ethanol, concentrating the filtrate to a paste, setting the temperature to 60° C. for drying, crushing by decompression, and sieving by a 40-mesh sieve to obtain an extract A; and processing the *Paeonia lactiflora* Pall. in the same way to obtain an extract B;

S3: adding the *Gardenia jasminoides* Ellis into a 80% ethanol aqueous solution with a volume ratio of material to liquid being 1:8, extracting twice for 1.5 hours each time, merging the extracting solutions, filtering, reclaiming ethanol, concentrating the filtrate to a paste, setting the temperature to 60° C. for drying, crushing by decompression, and sieving by a 40-mesh sieve to obtain an extract C;

S4: adding the *Albizia julibrissin* Durazz. into water with a volume ratio of material to liquid being 1:8, decocting twice for 1 hour each time, merging the decocting solutions, filtering, setting the temperature to 60° C.-65° C., concentrating the filtrate to a paste with a relative density of 1.10-1.12, stirring and adding an ethanol solution containing 50% of ethanol after natural cooling to room temperature, standing for 24 hours, taking the supernatant, filtering, reclaiming ethanol, concentrating the filtrate to a paste with a relative density of 1.28-1.30, setting the temperature to 60° C. for drying, crushing by decompression, and sieving by a 40-mesh sieve to obtain an extract D;

S5: adding the *Moutan cortex* into water with a volume ratio of material to liquid being 1:14, controlling the flow rate of distillate to be 6 mL·min-1 for every 200 g of medicinal materials, distilling for 5 hours, collecting the distillate and placing in a refrigerator at 4° C., refrigerating for 24 hours, crystallizing, conducting suction filtration, and drying the obtained crystal at 40° C.-45° C. to obtain an extract E; and S3: grinding and mixing the obtained extracts A-E at a weight ratio of 15:14:7:5:0.6 uniformly, and sieving by an 80-mesh pharmacopoeia sieve to obtain an antidepressant compound preparation.

Preferably, dosage forms of finished products include but are not limited to tablets, granules, powder, decoction, dripping pills, extractum and syrup.

It can be known from the above technical solution that compared with the prior art, the present invention has the following beneficial effects:

1. The present invention creates a traditional Chinese medicine compatibility composition and a preparation method therefor, and accurately proportions the weight components of *Hypericum perforatum* L., *Paeonia lactiflora* Pall., *Gardenia jasminoides* Ellis, *Albizia julibrissin* Durazz. and *Moutan cortex;*

2. The traditional Chinese medicine compound preparation and the preparation method therefor disclosed by the present invention have good effects on treating and alleviating depression mood, and the formula of pure traditional Chinese medicine has the advantages of safety, low toxic and side effects, no dependence, etc.;

3. In the traditional Chinese medicine compound preparation disclosed by the present invention, when the *Hypericum perforatum* L. is applied in combination with the traditional Chinese medicine composition of the present invention, the *Hypericum perforatum* L. can significantly enhance the interest of a mice in the external environment, which shows a significant antidepressant activity equivalent or even better than the single ingredient of *Hypericum perforatum* L., reflects a synergistic effect of the *Hypericum perforatum* L. and the traditional Chinese medicine composition in the solution, is helpful for alleviating depression mood, and has an antidepressant tendency.

DETAILED DESCRIPTION

The technical solution in embodiments of the present invention will be clearly and fully described below. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1

Embodiment 1 of the present invention discloses an antidepressant compound preparation and a preparation method therefor, and adopts the following technical solution:

An antidepressant compound preparation, composed of the following raw materials in parts by weight:

30 parts of *Hypericum perforatum* L., 120 parts of *Paeonia lactiflora* Pall., 60 parts of *Gardenia jasminoides* Ellis, 100 parts of *Albizia julibrissin* Durazz. and 100 parts of *Moutan cortex.*

Embodiment 2

Embodiment 2 of the present invention discloses an antidepressant compound preparation and a preparation method therefor, and adopts the following technical solution:

An antidepressant compound preparation, composed of the following raw materials in parts by weight:

20 parts of *Hypericum perforatum* L., 120 parts of *Paeonia lactiflora* Pall., 60 parts of *Gardenia jasminoides* Ellis, 100 parts of *Albizia julibrissin* Durazz. and 100 parts of *Moutan cortex.*

Embodiment 3

Embodiment 3 of the present invention discloses an antidepressant compound preparation and a preparation method therefor, and adopts the following technical solution:

An antidepressant compound preparation, composed of the following raw materials in parts by weight:

20 parts of *Hypericum perforatum* L., 120 parts of *Paeonia lactiflora* Pall., 60 parts of *Gardenia jasminoides* Ellis, 300 parts of *Albizia julibrissin* Durazz. and 100 parts of *Moutan cortex.*

Embodiment 4

Embodiment 4 of the present invention discloses an antidepressant compound preparation and a preparation method therefor, and adopts the following technical solution:

An antidepressant compound preparation, composed of the following raw materials in parts by weight:

50 parts of *Hypericum perforatum* L., 150 parts of *Paeonia lactiflora* Pall., 100 parts of *Gardenia jasminoides* Ellis, 250 parts of *Albizia julibrissin* Durazz. and 200 parts of *Moutan cortex.*

Embodiment 5

Embodiment 5 of the present invention discloses an antidepressant compound preparation and a preparation method therefor, and adopts the following technical solution:

An antidepressant compound preparation, composed of the following raw materials in parts by weight:

30 parts of *Hypericum perforatum* L., 120 parts of *Paeonia lactiflora* Pall., 60 parts of *Gardenia jasminoides* Ellis, 100 parts of *Albizia julibrissin* Durazz. and 150 parts of *Moutan cortex.*

Obtained extracts of *Hypericum perforatum* L., *Paeonia lactiflora* Pall., *Gardenia jasminoides* Ellis, *Albizia julibrissin* Durazz. and *Moutan cortex* are mixed uniformly, concentrated to a relative density of 1.08-1.10, and spray dried to obtain a medicinal powder; and the medicinal powder is sieved by a 40-mesh sieve, added with pregelatinized starch, talcum powder and magnesium stearate, mixed uniformly, capsuled, and made into capsules.

Embodiment 6

Embodiment 6 of the present invention discloses an antidepressant compound preparation and a preparation method therefor, and adopts the following technical solution:

An antidepressant compound preparation, composed of the following raw materials in parts by weight:

30 parts of *Hypericum perforatum* L., 120 parts of *Paeonia lactiflora* Pall., 60 parts of *Gardenia jasminoides* Ellis, 100 parts of *Albizia julibrissin* Durazz. and 100 parts of *Moutan cortex*.

Obtained extracts of *Hypericum perforatum* L., *Paeonia lactiflora* Pall., *Gardenia jasminoides* Ellis, *Albizia julibrissin* Durazz. and *Moutan cortex* are mixed uniformly, concentrated to a relative density of 1.08-1.10, and spray dried to obtain a medicinal powder; and the medicinal powder is sieved by a 40-mesh sieve, added with starch and magnesium stearate, mixed uniformly, compressed into tablets, coated with film, and made into tablets.

Embodiment 7

Embodiment 7 of the present invention discloses an antidepressant compound preparation and a preparation method therefor, and adopts the following technical solution:

An antidepressant compound preparation, composed of the following raw materials in parts by weight:

10 parts of *Hypericum perforatum* L., 100 parts of *Paeonia lactiflora* Pall., 10 parts of *Gardenia jasminoides* Ellis, 100 parts of *Albizia julibrissin* Durazz. and 50 parts of *Moutan cortex*.

Obtained extracts of *Hypericum perforatum* L., *Paeonia lactiflora* Pall., *Gardenia jasminoides* Ellis, *Albizia julibrissin* Durazz. and *Moutan cortex* are mixed uniformly, and decocted to 1 g/mL; and decocted extractum is placed in a beaker, added with cane sugar, starch and dextrin, mixed uniformly, kneaded into balls that will disperse at one touch, sieved by a 10-mesh sieve, vacuum dried with the water content of particles controlled to be 4%, and made into granules.

Embodiment 8

To test the curative effect of the compound preparation prepared by the present invention, 40 SPF grade male Kunming mice are selected with 4-5 mice in each cage, allowed to acclimate for 1 week, and divided into 4 groups with 10 mice in each group according to a randomized block design method. The first group is a normal control group, the second group is a *Morinda officinalis* How. oligosaccharide capsule group, the third group is a *Hypericum perforatum* L. tablet group, and the fourth group is a compound traditional Chinese medicine group. The mice are treated by gavage at a fixed time every morning for one month, and are tested 1 hour after the last gavage. The test results are recorded.

(1) Mouse Elevated Plus Maze Test

An elevated plus maze is designed, which comprises 2 relatively open arms of 35 cm×6 cm and 2 relatively closed arms of 35 cm×6 cm. The upper part of each closed arm is open, the four sides of each open arm are open, and a relatively open area of 5 cm×5 cm is formed in the center among the open arms and the closed arms. The maze is 50 cm above the ground. The mice are placed in the central open area with the heads facing the closed arms. The number of open arm entries and closed arm entries of the mice within 5 minutes and the residence time in the open and closed arms are recorded by a software (the standard is that the limbs of each mouse are completely in or out of the arms).

The percentages (proportions) of the number of open arm entries of the mice and the residence time in the open arms in (to) the total number (the sum of the numbers of open arm entries and closed arm entries) and the total residence time (the sum of the residence time in the open and closed arms) respectively are calculated.

(2) Mouse Forced Swimming Depression Model Test

All the mice are respectively put in a plexiglass cylinder with a water temperature of 23° C. and a water depth of 20 cm. After 15 minutes, the mice are transferred to a dry environment with a temperature of 30° C. and kept for 30 minutes (pretest). After 24 hours, the mice are put into the plexiglass cylinder again and kept for 5 minutes (formal test). A video camera is used during the test for recording. After each mouse is tested, the water is changed and the cylinder is cleaned, and the floating immobility time is recorded by a software.

(3) Mouse Nembutal (with Dose Above Threshold) Synergistic Hypnosis Test

After 1 hour from the last gavage of the mice, each group of mice are treated by intraperitoneal injection of 40 mg·kg$^{-1}$ of nembutal (a proposed dose is found by a pretest), the mice are placed on a warm hot plate with a temperature of 37° C., and the time when the righting reflex disappears (the standard is that the righting reflex disappears for more than 1 minute) and the sleeping time of the mice are observed and recorded.

The test results of the mouse elevated plus maze test are as follows:

TABLE 1

Effect of Drug to be Tested on OE % in Mouse Elevated Plus Maze Test ($\bar{x} \pm$ SE)

| Groups | Dose | Number of animals | OE % |
|---|---|---|---|
| Control group | — | 10 | 0.3527 ± 0.05774 |
| *Morinda officinalis* How. oligosaccharide capsule group | 285 mg/kg | 10 | 0.3853 ± 0.0583 |
| *Hypericum perforatum* L. tablet group | 280 mg/kg | 10 | 0.3684 ± 0.04086 |
| Compound traditional Chinese medicine group | 2.07 g/kg | 10 | 0.3443 ± 0.03184 |

TABLE 2

Effect of Drug to be Tested on OT % in Mouse Elevated Plus Maze (EPM) Test ($\bar{x} \pm$ SE)

| Groups | Dose | Number of animals | OT % |
|---|---|---|---|
| Control group | — | 10 | 0.2547 ± 0.05522 |
| *Morinda officinalis* How. oligosaccharide capsule group | 285 mg/kg | 10 | 0.3781 ± 0.06311 |
| *Hypericum perforatum* L. tablet group | 280 mg/kg | 10 | 0.2947 ± 0.05947 |
| Compound traditional Chinese medicine group | 2.07 g/kg | 10 | 0.2328 ± 0.03232 |

Note:
compared with the control group, * $P < 0.05$.

The test results of the mouse forced swimming depression model test are as follows:

TABLE 3

Effect of Drug to be Tested on Floating Immobility Time in Mouse
Forced Swimming Test (FST) ($\bar{x} \pm SE$)

| Groups | Dose | Number of animals | Floating immobility time (second) |
|---|---|---|---|
| Control group | — | 10 | 31.87 ± 6.233 |
| Morinda officinalis How. oligosaccharide capsule group | 285 mg/kg | 10 | 33.28 ± 7.551 |
| Hypericum perforatum L. tablet group | 280 mg/kg | 10 | 20.23 ± 3.801 |
| Compound traditional Chinese medicine group | 2.07 g/kg | 10 | 24.59 ± 4.774 |

Note:
compared with the control group, * P < 0.05.

The test results of the mouse nembutal (with dose above threshold) synergistic hypnosis test are as follows:

TABLE 4

Effect of Drug to be Tested on Sleeping Latency in Mouse
Synergistic Hypnosis Test ($\bar{x} \pm SE$)

| Groups | Dose | Number of animals | Sleeping latency (second) |
|---|---|---|---|
| Control group | — | 10 | 945.4 ± 221.4 |
| Morinda officinalis How. oligosaccharide capsule group | 285 mg/kg | 10 | 411.8 ± 62.81* |
| Hypericum perforatum L. tablet group | 280 mg/kg | 10 | 409.1 ± 50.01* |
| Compound traditional Chinese medicine group | 2.07 g/kg | 10 | 327.7 ± 39.27** |

Note:
compared with the control group, *P < 0.05, and **p < 0.01.

TABLE 5

Effect of Drug to be Tested on Sleeping Time in Mouse
Synergistic Hypnosis Test ($\bar{x} \pm SE$)

| Groups | Dose | Number of animals | Sleeping time (second) |
|---|---|---|---|
| Control group | — | 10 | 1411 ± 301.4 |
| Morinda officinalis How. oligosaccharide capsule group | 285 mg/kg | 10 | 3365 ± 403.3*** |
| Hypericum perforatum L. tablet group | 280 mg/kg | 10 | 2321 ± 248.6* |
| Compound traditional Chinese medicine group | 2.07 g/kg | 10 | 3446 ± 634.4** |

Note:
compared with the control group, *P < 0.05, p < 0.01, and *p < 0.001.

Embodiment 9

The compound preparation prepared by embodiment 1 is taken as an example to test the curative effect thereof on depression mood.
Experimental Group and Administration
Experimental Group:
72 SPF grade male C57BL/6J mice which are 20±2 g in weight are selected. 6 mice are kept in each cage, free to forage and drink, and kept in a room with controlled light, temperature and humidity: the temperature is 21° C.±2° C., the humidity is 50%±10%, and the light and dark cycle is 12 hours/12 hours (light on at 20:00, light off at 8:00). All animal experiments are carried out in accordance with the guidelines on laboratory animal welfare and use issued by NIH.

After arrival, the mice are allowed to acclimate for one week before entering experiments. The mice are divided into 6 groups with 12 mice in each group according to a randomized block design method, and the groups include: a normal control group (Control), a fluoxetine group (FXT), a St. John's wort extract group (LQ), a compound traditional Chinese medicine low dose group (MH-2-L), a compound traditional Chinese medicine medium dose group (MH-2-M), and a compound traditional Chinese medicine high dose group (MH-2-H).

Administration Method and Course of Treatment:

The mice in the normal group are given the same volume of purified water by gavage, and the gavage doses for the mice in other groups are shown in the result tables. The mice are treated by gavage at a fixed time (9:00) every morning with a gavage volume of 0.1 mL·10 $g^{-1}$, and the administration is lasted for one month. A behavioral test is performed 1 hour after the last gavage.

Test Method:

(1) Mouse Open Field Test

The test is performed in an open field box with a length of 50 cm, a width of 50 cm, and a depth of 50 cm. The bottom surface of the open field box is equally divided into 9 squares, the area right in the middle is a central area, and the remaining areas are peripheral areas. The bottom and four sides of the open field box are all white. The test is performed in a quiet and weak red light environment. At the beginning, the mice are put in the center of the open field box, and activities within 6 minutes are observed. The total movement distance of the mice, the movement distance in the central area and the number of standing-uprights are recorded.

(2) Mouse Forced Swimming Test

When forced to swim, all the animals are respectively put in a plexiglass cylinder with a water temperature of 23° C.±1° C. and a water depth of 20 cm. After 15 minutes, the animals are transferred to a dry environment with a temperature of 30° C. and kept for 30 minutes (pretest). After 24 hours, the mice are put into the plexiglass cylinder again and kept for 5 minutes (formal test). A video camera is used during the test for recording. After each mouse is tested, the water is changed and the cylinder is cleaned. A SMART 3.0 software is used to record the number of floating immobilities and the latency of floating immobility.

(3) Mouse Tail Suspension Test

In the tail suspension test, medical tape is used to suspend each mouse at ⅓ of the tail tip on a tail suspension device. The mice are suspended vertically with the heads facing camera lens, and are about 30 cm above the ground. The immobility time of each group of mice in the tail suspension test is recorded by a video camera for 6 minutes, and the tail suspension immobility time of the mice is calculated according to the last 4 minutes. The immobility time is judged by that the mice stop struggling, hang upside down, and stand still.

Test Results:

The test results of the open field test are as follows:

TABLE 1

Effect of Drug to be Tested on Total Movement Distance in Mouse Open Field Test ($\bar{x} \pm SE$)

| Groups | Dose | Number of animals | Total movement distance (mm) |
|---|---|---|---|
| Control group | 0 | 9 | 19083 ± 1395 |
| Fluoxetine group | 3.33 mg/kg | 10 | 18435 ± 950.6 |
| St. John's wort extract group | 186.67 mg/kg | 10 | 19151 ± 1678 |
| MH-2 low dose group | 176.75 mg/kg | 10 | 18447 ± 1621 |
| MH-2 medium dose group | 353.5 mg/kg | 10 | 18866 ± 1141 |
| MH-2 high dose group | 707 mg/kg | 9 | 18600 ± 1221 |

TABLE 2

Effect of Drug to be Tested on Movement Distance in Central Area in Mouse Open Field Test ($\bar{x} \pm SE$)

| Groups | Dose | Number of animals | Movement distance in central area (mm) |
|---|---|---|---|
| Control group | 0 | 9 | 1285 ± 112.2 |
| Fluoxetine group | 3.33 mg/kg | 10 | 1167 ± 126.6 |
| St. John's wort extract group | 186.67 mg/kg | 10 | 1377 ± 117.3 |
| MH-2 low dose group | 176.75 mg/kg | 10 | 1195 ± 167.3 |
| MH-2 medium dose group | 353.5 mg/kg | 10 | 1331 ± 162.5 |
| MH-2 high dose group | 707 mg/kg | 9 | 1029 ± 139.7 |

TABLE 3

Effect of Drug to be Tested on Number of Standing-Uprights in Mouse Open Field Test ($\bar{x} \pm SE$)

| Groups | Dose | Number of animals | Number of standing-uprights |
|---|---|---|---|
| Control group | 0 | 9 | 27.89 ± 1.654 |
| Fluoxetine group | 3.33 mg/kg | 10 | 29.20 ± 2.133 |
| St. John's wort extract group | 186.67 mg/kg | 10 | 30.00 ± 2.777 |
| MH-2 low dose group | 176.75 mg/kg | 10 | 25.90 ± 2.116 |
| MH-2 medium dose group | 353.5 mg/kg | 10 | 33.10 ± 2.063* |
| MH-2 high dose group | 707 mg/kg | 9 | 26.44 ± 2.381 |

Note:
compared with the control group, *P < 0.05.

After administration by gavage, the number of standing-uprights in the MH-2 medium dose group is significantly higher than that in the normal control group, which indicates that after MH-2 medium dose administration, the exploratory activities of the mice can be enhanced, and the interest of the mice in the external environment can be increased.

The test results of the forced swimming test are as follows:

TABLE 4

Effect of Drug to be Tested on Number of Floating Immobilities in Mouse Forced Swimming Test ($\bar{x} \pm SE$)

| Groups | Dose | Number of animals | Number of floating immobilities |
|---|---|---|---|
| Control group | 0 | 11 | 65.55 ± 4.611 |
| Fluoxetine group | 3.33 mg/kg | 11 | 54.64 ± 2.704* |
| St. John's wort extract group | 186.67 mg/kg | 12 | 45.25 ± 4.695** |
| MH-2 low dose group | 176.75 mg/kg | 11 | 56.64 ± 6.359 |
| MH-2 medium dose group | 353.5 mg/kg | 11 | 55.73 ± 3.171* |
| MH-2 high dose group | 707 mg/kg | 11 | 50.09 ± 5.691* |

Note:
compared with the control group, *P < 0.05, and **p < 0.01.

After administration by gavage, the number of floating immobilities in each of the fluoxetine group, the St. John's wort extract group, the MH-2 medium dose group and the MH-2 high dose group is significantly lower than that in the normal control group, which indicates that the intervention of fluoxetine, St. John's wort extract, and MH-2 medium and high doses can significantly alleviate the "behavioral despair" state of the mice and reduce the number of floating immobilities.

The test results of the tail suspension test are as follows:

TABLE 5

Effect of Drug to be Tested on Tail Suspension Immobility Time in Mouse Tail Suspension Test ($\bar{x} \pm SE$)

| Groups | Dose | Number of animals | Tail suspension immobility time (second) |
|---|---|---|---|
| Control group | 0 | 11 | 81.37 ± 5.817 |
| Fluoxetine group | 3.33 mg/kg | 10 | 59.62 ± 6.270** |
| St. John's wort extract group | 186.67 mg/kg | 9 | 64.53 ± 7.152* |
| MR-2 low dose group | 176.75 mg/kg | 10 | 70.70 ± 6.520 |
| MH-2 medium dose group | 353.5 mg/kg | 9 | 52.77 ± 9.259** |
| MR-2 high dose group | 707 mg/kg | 12 | 64.07 ± 5.689* |

Note:
compared with the control group, *P < 0.05, and **p < 0.01.

After administration by gavage, the tail suspension immobility time in each of the fluoxetine group, the St. John's wort extract group, the MH-2 medium dose group and the MH-2 high dose group is significantly shorter than that in the normal control group, which indicates that the intervention of fluoxetine, St. John's wort extract, and MH-2 medium and high doses can significantly alleviate the "behavioral despair" state of the mice and shorten the tail suspension immobility time.

Based on the analysis of the above test results, the fluoxetine, the St. John's wort extract, the MH-2 medium dose and the MH-2 high dose can significantly reduce the number of floating immobilities or shorten the tail suspension immobility time, showing a significant antidepressant activity. The exploratory activities of the mice in the MH-2 medium dose group can also be significantly enhanced, and the interest of the mice in the external environment can be increased. The antidepressant-related parameters of multiple behavior models in the MH-2 medium dose group can be significantly improved.

Embodiment 10

(1) Acute Toxicity

Acute toxicity test by mouse gavage (maximum tolerance measurement method): 10 male and 10 female mice are selected. A solution of 0.5 g/mL is prepared as a sample, and the administration dose is 1 mL/20 g. The mice in a blank control group are fed with 0.9% sodium chloride injection of 1 mL/20 g body weight, treated by gavage twice with an interval of 4 hours, and observed for 14 days. During the test, the animals have normal activity, normal weight gain and no adverse reactions, and mortality rate of the animals is 0%.

(2) Long-Term Toxicity Test:

80 SD rats with fifty-fifty males and females are selected and kept in separate cages. The rats are randomly divided into four groups with 20 rats in each group, and the groups include: a control group, a low dose group (10.155 g/kg), a medium dose group (23.695 g/kg), and a high dose group (33.85 g/kg). Drug is administrated 6 days a week, discontinued 1 day, and continuously administered for 3 months. Appearance, physical signs, behaviors, activities, glandular secretion, respiration, feces, etc. of the animals are observed every day. During the test, all the indexes of the animals are normal, and the animals have no adverse reactions.

Each embodiment in the description is described in a progressive way. The difference of each embodiment from each other is the focus of explanation. The same and similar parts among all of the embodiments can be referred to each other.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention.

Therefore, the present invention will not be limited to these embodiments shown herein, but will conform to the widest scope consistent with the principle and novel features disclosed herein.

We claim:

1. A method for preparing an antidepressant compound, comprising:

S1: weighing *Hypericum perforatum* L., *Paeonia lactiflora* Pall., *Gardenia jasminoides* Ellis, *Albizia julibrissin* Durazz. and *Moutan cortex* in proportion to prepare materials;

S2: adding the *Hypericum perforatum* L. into a 70% ethanol aqueous solution with a volume ratio of the material to liquid being 1:8, extracting twice for 1.5 hours each time, merging the extracting solutions, filtering, reclaiming ethanol, concentrating the filtrate to a paste, setting the temperature to 60° C. for drying, crushing by decompression, and sieving by a 40-mesh sieve to obtain an extract A; and processing the *Paeonia lactiflora* Pall. in the same way to obtain an extract B;

S3: adding the *Gardenia jasminoides* Ellis into a 80% ethanol aqueous solution with a volume ratio of the material to liquid being 1:8, extracting twice for 1.5 hours each time, merging the extracting solutions, filtering, reclaiming ethanol, concentrating the filtrate to a paste, setting the temperature to 60° C. for drying, crushing by decompression, and sieving, by a 40-mesh sieve to obtain an extract C;

S4: adding the *Albizia julibrissin* Durazz. into water with a volume ratio of the material to liquid being 1:8, decocting twice for 1 hour each time, merging the decocting solutions, filtering, setting the temperature to 60° C.-65° C., concentrating the filtrate to a paste with a relative density of 1.10-1.12, stirring and adding an ethanol solution containing 50% of ethanol after natural cooling to room temperature, standing for 24 hours, taking the supernatant, filtering, reclaiming ethanol, concentrating the filtrate to a paste with a relative density of 1.28-1.30, setting the temperature to 60° C. for drying, crushing by decompression, and sieving by a 40-mesh sieve to obtain an extract D;

S5: adding the *Moutan cortex* into water with a volume ratio of material to the liquid being 1:14, controlling the flow rate of distillate to be 6 mL·min−1 for every 200 g of medicinal materials, distilling for 5 hours, collecting the distillate and placing in a refrigerator at 4° C., refrigerating for 24 hours, crystallizing, conducting suction filtration, and drying the obtained crystal at 40° C.-45° C. to obtain an extract E; and S3: grinding and mixing the obtained extracts A-E, at a weight ratio of 15:14:7:5:0.6 uniformly, and sieving by an 80-mesh pharmacopoeia sieve to obtain an antidepressant compound.

* * * * *